United States Patent
Renk

[19]

[11] Patent Number: 6,037,580
[45] Date of Patent: Mar. 14, 2000

[54] SAFETY DEVICE FOR COOKING APPLIANCE

[75] Inventor: Rémi Renk, Remiremont, France

[73] Assignee: SEB S.A., Ecully, France

[21] Appl. No.: 08/944,966

[22] Filed: Oct. 7, 1997

[30] Foreign Application Priority Data

Oct. 9, 1996 [FR] France ................................. 96 12522

[51] Int. Cl.[7] .......................... A47J 37/08; G08B 17/113; H05B 1/02
[52] U.S. Cl. ................. 250/221; 250/222.1; 250/214 B; 250/573; 219/490; 219/502; 99/325; 99/337; 99/385
[58] Field of Search ................................ 250/221, 222.1, 250/214 B, 573, 338.1, 338.4, 339.03, 339.05, 341.1, 345; 219/502, 509, 518, 490, 507; 99/385, 324, 325, 326, 327, 328, 337, 338

[56] References Cited

U.S. PATENT DOCUMENTS

| | | |
|---|---|---|
| 4,199,755 | 4/1980 | Tanaka . |
| 4,749,871 | 6/1988 | Galvin et al. ............................ 250/573 |
| 4,976,194 | 12/1990 | Kelterborn et al. .................... 219/502 |
| 5,373,145 | 12/1994 | Endo et al. ............................... 99/328 |
| 5,486,685 | 1/1996 | Dodds ..................................... 219/518 |
| 5,493,119 | 2/1996 | Torngren . |
| 5,574,435 | 11/1996 | Mochizuki .............................. 250/573 |
| 5,698,845 | 12/1997 | Kodama et al. ........................ 250/221 |
| 5,819,637 | 10/1998 | Botma et al. ............................. 99/327 |

FOREIGN PATENT DOCUMENTS

| | | |
|---|---|---|
| 0 729 024 | 8/1996 | European Pat. Off. . |
| 2 609 342 | 7/1988 | France . |
| 42 43 004 | 6/1993 | Germany . |
| 2 095 821 | 10/1982 | United Kingdom . |
| 2 261 502 | 5/1993 | United Kingdom . |

Primary Examiner—John R. Lee
Attorney, Agent, or Firm—Pillsbury Madison & Sutro

[57] ABSTRACT

Safety device composed of a radiation emitter, a radiation receiver disposed for receiving radiation which is produced by the emitter and which traverses a radiation path between the emitter and the detector, the detector producing an output signal representative of the quantity of radiation received by the detector, and an electronic circuit coupled to the detector for analyzing the output signal produced by the detector and identifying a reduction in the magnitude of the output signal as a result of an obstruction in the radiation path, wherein the emitter and the detector are mounted on a cooking appliance in a manner which allows extraneous radiation in the vicinity of the cooking appliance to traverse the radiation path.

28 Claims, 5 Drawing Sheets

SAFETY DEVICE FOR COOKING APPLIANCE

BACKGROUND OF THE INVENTION

The present invention relates to the general field of household electric appliances, and more particularly cooking appliances of the oven or toaster type.

The present invention concerns a safety device permitting, in particular, the detection of smoke and of performance of a certain number of functions relating to operating safety of the appliances under various utilization conditions.

The present invention thus permits construction of a device for detection of smoke as well as bodies having a certain opacity to light, these including objects and a user's hand, and capable of controlling the operation of household electric appliances, of the toaster type, by initiating a stop-eject function or interruption of the supply of current to heating elements.

It is already known to provide smoke detection devices for use in microwave ovens. Thus, U.S. Pat. No. 5,493,119 describes a detector for the presence of smoke or vapors, or fumes, in a microwave chamber. The detector comprises a light emitting diode as well as two optical receivers of the phototransistor type, permitting reception of a signal by transmission, reflection or diffusion when smoke or steam passes through the detector, and more precisely through the detector analysis chamber, this chamber being isolated optically with respect to ambient light or any other parasitic light source. This document also describes analyzing electronics for recognizing an increase in the intensity of the signal on one of the detectors and simultaneously a decrease in the intensity of the signal on the other detector.

Such a detector presents the drawback of not being able to operate correctly or in an effective manner when it is subjected to parasitic light or radiation. Its precise positioning, sheltered from all parasitic radiation, is thus indispensable. This gives rise to particular mounting constraints, and increased fabrication costs, to the extent that smoke must be channeled and brought into a detection chamber.

It is also known, as disclosed in French Patent Document FR-A-2 609 342, to provide a device which includes a chamber into which smoke penetrates, a light emitting diode and a phototransistor. This document also describes means permitting development of an outlet signal from the phototransistor, this being for the purpose of detecting attenuation of a signal emitted by the light emitting diode. Such a device presents the disadvantage that it comprises an analysis chamber in which an optical system is arranged, this being for the purpose of preventing the influence of ambient or parasitic light on the photodiode or the optical receptor. Another disadvantage resulting therefrom is that the smoke must be channeled and led into the analysis chamber.

BRIEF SUMMARY OF THE INVENTION

A first object of the present invention is to overcome the prior art drawbacks discussed above and to provide a smoke detection device which is effective and provides a rapid response in cooking appliances.

A second object of the present invention is to discontinue the supply of electric current to the heating means of a cooking appliance upon detection of a body or object close to the cooking chamber where it could hinder free circulation of air outside of this cooking chamber, thereby provoking serious consequences for the operation of the appliance due to overheating, possibly leading to the start of a fire.

Another object of the present invention concerns protection of the user on the occasion of a dangerous handling of the appliance when a cooking cycle is in progress. In effect, the user, in handling the appliance or attempting to introduce their hand or a metal object, risks being burned, or, which can be more serious, being electrocuted. Thus, the safety device according to the invention prevents all risk of electrocution by terminating the supply of energy to the heating means well before any object or the hand of the user can come in contact with elements which are under a high voltage. In addition, together with this termination of energy supply, the bread transporting carriage is freed from its toasting position, triggering a noise which can be reinforced by an alarm, this noise being capable of inducing in the user a reflexive withdrawal of their hand.

An object of the present invention is thus to provide an optical system which can function reliably even when exposed to ambient radiation, by eliminating signals resulting from such ambient radiation, in a manner to monitor or control the operation of an appliance.

Another object of the present invention is to achieve the totality of these functions with inexpensive means which can be implemented in a simple manner.

Another object of the present invention is to provide an optical safety device which in particular permits detection of smoke, without, for this purpose, utilizing an analyzing chamber which is isolated from ambient radiation.

The above and other objects according to the invention are achieved with the aid of an optical safety device comprising at least one optical emitter, at least one optical detector and electronic means for analyzing a signal received by the optical detector by recognizing a decrease in the intensity of the signal due to an obstruction of the optical path followed by the signal, wherein the optical detector and emitter are mounted on a cooking appliance in a manner to not be optically isolated from the device and/or the optical path, with respect to radiation in the vicinity of the cooking appliance.

Objects according to the invention are further achieved by a method for detecting the presence of a body having a certain opacity, which method includes recognizing the attenuation of an optical signal due to an obstruction of the optical path followed by the signal and monitoring the operation of an appliance in response to such detection, wherein the method further includes:

utilizing optical radiation which at least partially traverses a cooking environment, utilizing an optical emitter permitting the generation of a pulsed optical signal, and utilizing an optical receptor associated with filter means for filtering and isolating the signal received by the detector.

Other advantages and characteristics of the invention will appear more clearly from a reading of the following description, which refers to the attached drawings, relating to non-limiting examples of the invention.

DETAILED DESCRIPTION OF THE INVENTION

Figure 1:
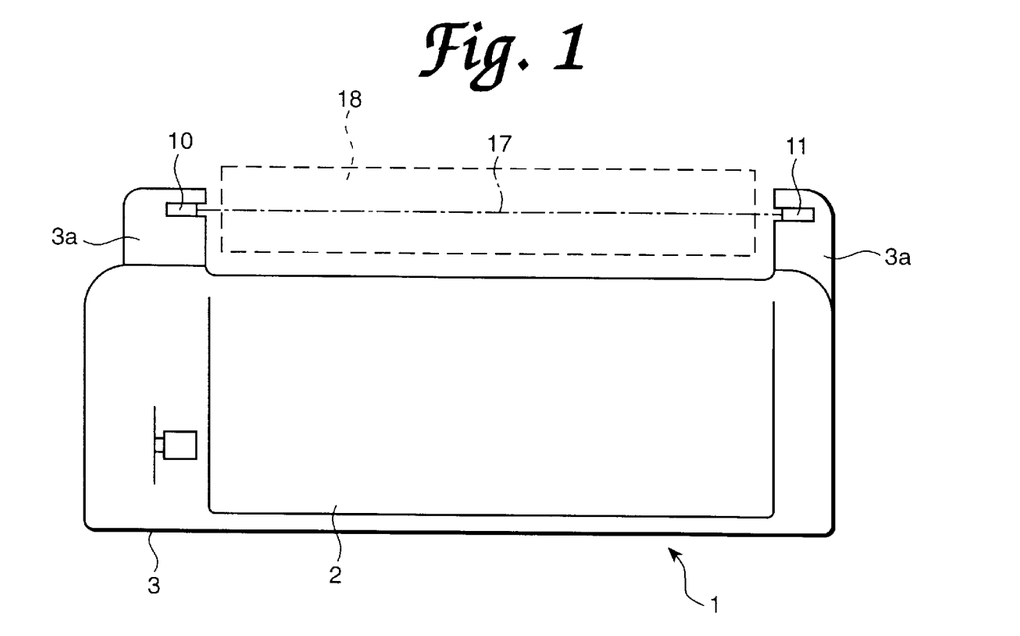
FIG. 1 is a simplified elevational view of a toaster equipped with a device according to the invention.

FIG. 1 is a simplified elevational view of a cooking appliance, the illustrated appliance being, simply by way of example, a toaster 1 of the pop-up type. Toaster 1 is composed basically of a housing 3 containing a chamber 2, which in this case is a toasting or grilling chamber intended to receive one or more slices of bread to be toasted.

Housing 3 also includes upwardly extending, or raised, components 3a disposed at opposite ends of toaster 1, and more specifically adjacent opposite ends of the bread receiving opening associated with chamber 2. One of the components 3a houses a radiation emitter 10, while the other one of components 3a houses a radiation receiver 11. Radiation emitted by emitter 10 travels to receiver 11 via a path 17 which is substantially transparent to the radiation. Path 17 is positioned above chamber 2, and in particular above the bread receiving opening associated with chamber 2.

Other locations for emitter 10 and receiver 11 can be selected without departing from the spirit of the present invention. It is thus possible to dispose emitter 10 and receiver 11 in a manner to define a path 17 across the width of chamber 2. Emitter 10 and receiver 11 are thus mounted on toaster 1 in a manner which is not isolated from radiation in the vicinity of the appliance. The optical system utilized in embodiments of the present invention is effectively disposed at a location where the influence of ambient light or parasitic or interfering radiation cannot be avoided.

Advantageously, path 17 extends in the direction of the largest dimension of toaster 1. According to other embodiments, several emitter-receiver pairs can easily be arranged on housing 3. Advantageously, several emitter-receiver sets can be disposed to have optical paths which extend perpendicular to the largest dimension of the bread receiving opening, or slot, of a toaster.

Preferably, emitter 10 and receiver 11 are disposed in a manner such that path 17 extends across the cooking environment of the appliance, and in particular toaster 1. The term "cooking environment" is intended to identify the internal volume of chamber 2 or a space situated in the vicinity of chamber 2, and preferably thereabove. Such a space will be traversed by smoke or other vapors produced during cooking or toasting. The safety device according to the invention thus includes a radiation sensing system arranged in the vicinity of a column of hot air 18 which is localized to the vicinity of a cooking environment, as shown particularly in FIGS. 1 and 6. By disposing this safety system above the cooking chamber, in the flow of hot air exiting from the cooking chamber, it is possible for the device to detect smoke or other vapors exiting the appliance. In addition, the insertion of any object, for example the user's hand, into the interior of the cooking enclosure during a cooking cycle can provoke an immediate halt in the operation of the appliance.

Preferably, the radiation system includes a focussing arrangement 14 or a collimation arrangement 15 associated with a diaphragm 16, diaphragm 16 being disposed in front of receiver 11. Receiver 11 is connected to an electronic circuit 20 (FIGS. 6, 9 and 10) which processes the signal produced by receiver 11 to produce an indication when the intensity of the radiation on path 17 decreases upon the appearance of an obstruction in path 17 along which the detected radiation has traveled.

Figure 6:
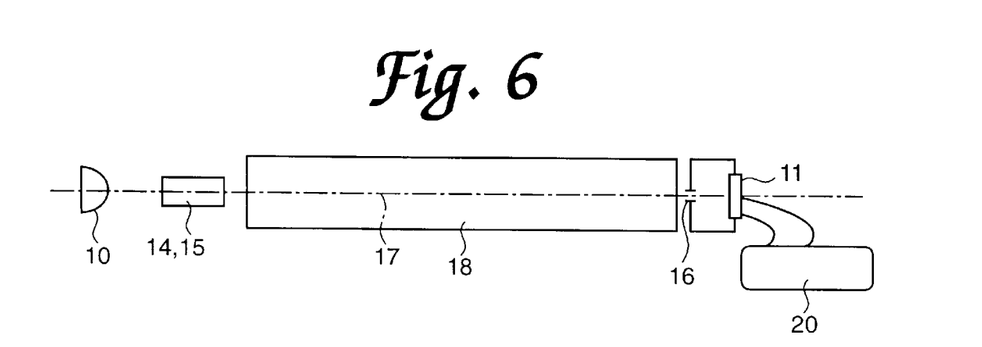
FIGS. 6, 7, 8, 9 and 10 are pictorial views illustrating different embodiments of an optical system employed in a device according to the invention.

FIG. 6 shows one example of an optical system utilized in a safety device according to the invention. Two alternative versions of the optical system are shown in FIGS. 7 and 8.

Figure 7:
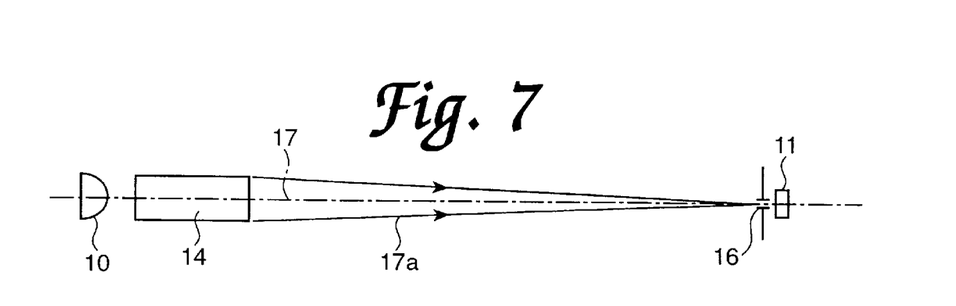

In the optical system shown in FIG. 7, path 17 constitutes the longitudinal axis of a radiation beam 17a which passes through diaphragm 16 in order to reach the radiation sensing surface, or element, of receiver 11. Beam 17a is formed into a converging beam which is focussed on the opening in diaphragm 16 or on receiver 11 as a result of its passage through focussing arrangement 14.

Figure 8:
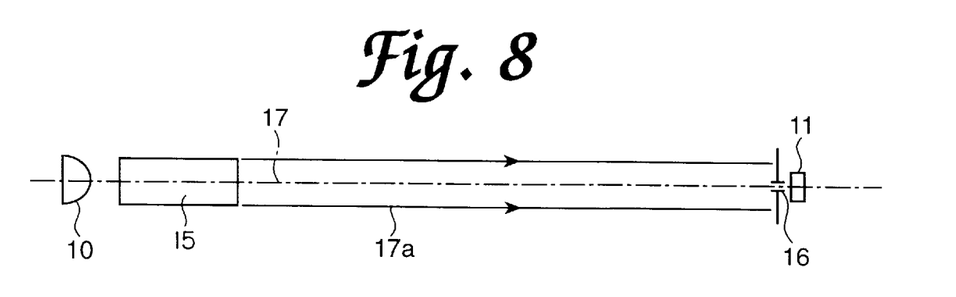

In the embodiment shown in FIG. 8, radiation emitted by emitter 10 passes through collimation arrangement 15, which gives the radiation the form of a collimated beam 17a parallel to, and enclosing, path 17.

Figure 9:
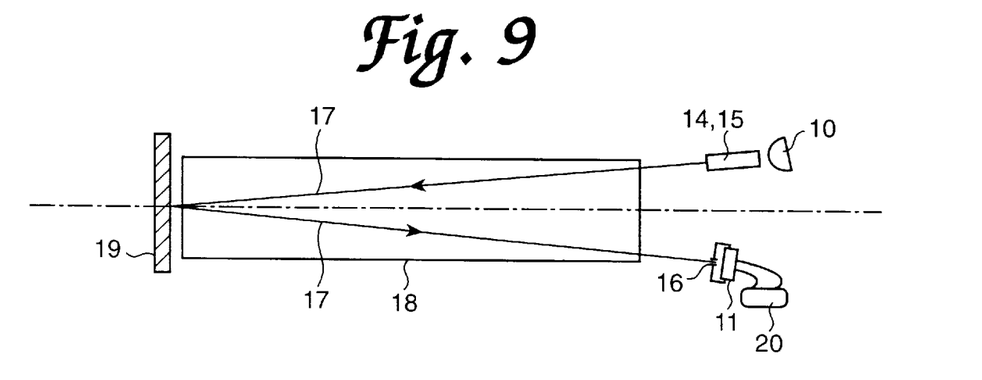

Referring to FIG. 9, it is also possible to provide a mirror 19, or other type of reflecting surface, in path 17. The resulting configuration of path 17 allows emitter 10 and receiver 11 to be disposed, for example, at the same side, or end, of the cooking appliance, such as toaster 1. An embodiment of the type shown in FIG. 9 can include a focussing arrangement 14 or a collimation arrangement 15 and diaphragm 16. In a variation of the embodiment shown in FIG. 9, emitter 10 and receiver 11 can be disposed essentially side-by-side so that the angle between the two parts of path 17 is practically zero.

Figure 10:
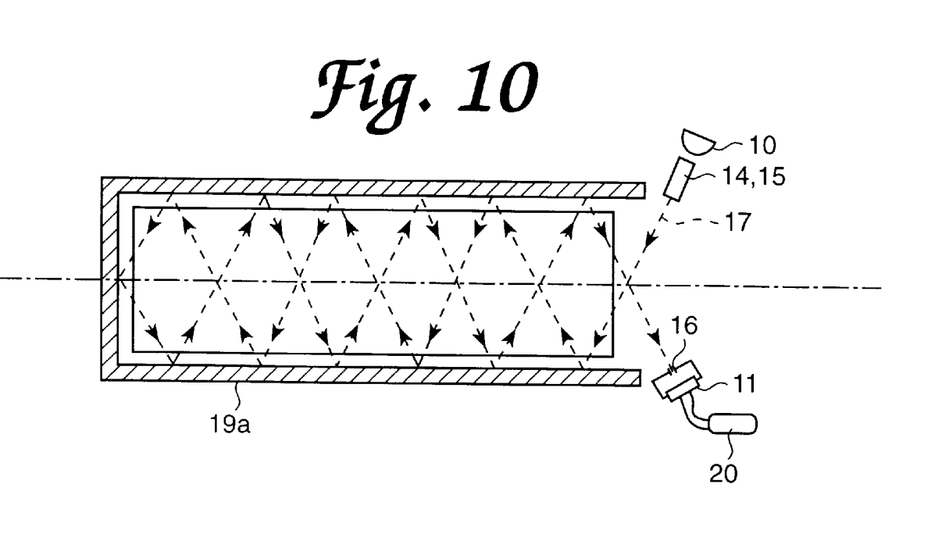

FIG. 10 shows another exemplary embodiment of an optical system for use in a device according to the invention. In this embodiment, path 17 is formed by a series of reflections on a set of reflective walls. As a result, path 17 traces a comparatively complex path which allows a larger area to be monitored in a complete manner. The reflecting surfaces are provided by a mirror system 19a which can have a variety of more or less complex configurations. Mirror system 19a shown in FIG. 10 is, for example, constituted by a reflecting material presenting three reflecting surfaces enclosing an area corresponding to the cross-sectional area of the bread receiving opening of toaster 1.

Figure 2:
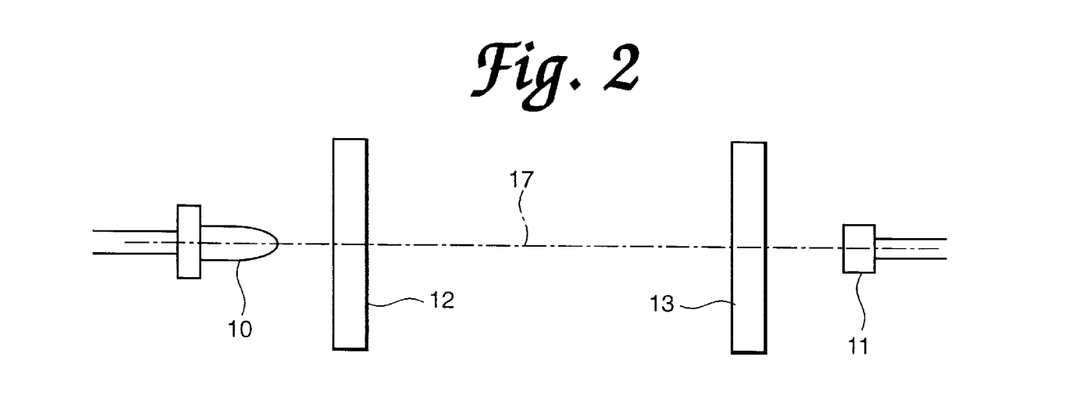
FIG. 2 is a pictorial view of an exemplary embodiment of an optical system employed in a device according to the invention.

Another embodiment of an optical system integrated into a safety device according to the invention is shown in FIG. 2. In this embodiment, emitter 10 and receiver 11 are associated with a polarizer 12 and an analyzer 13, both of which extend across path 17. Polarizer 12 and analyzer 13 thus permit filtering of the radiation signal emitted by emitter 10 by polarizing the emitted radiation and detecting, in receiver 11, a radiation signal having the same polarization as that emerging from polarizer 12. Such a system thus permits the influence of parasitic radiation to be reduced. Other known radiation filtering means, such as color filters, can equally be utilized without departing from the spirit of the present invention.

Figure 11:
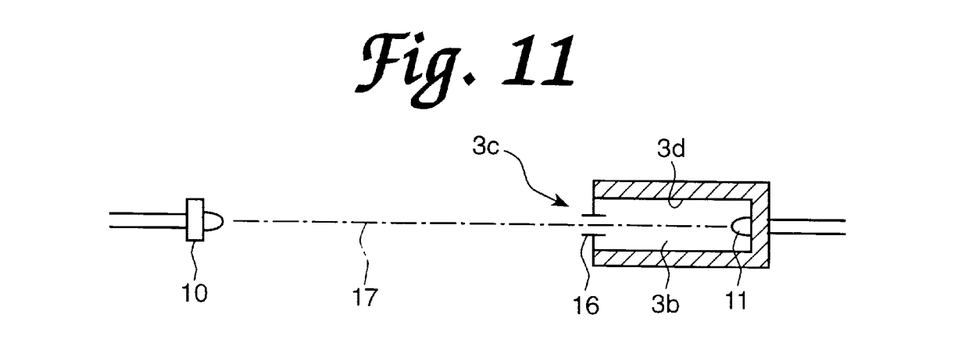
FIG. 11 is a pictorial view, partly in cross section, of a preferred embodiment of the optical system of a device according to the invention.

Another embodiment of a device according to the invention is shown in FIG. 11 in which receiver 11 is mounted at the bottom of a blind bore formed in a cup-shaped member 3b. Member 3b has an opening 3c which is preferably associated with a diaphragm 16 in a manner to limit the parasitic radiation arriving on the sensing surface of receiver 11. Alternatively, opening 3c can be dimensioned to itself form the diaphragm. Member 3b preferably has an internal wall 3d which is made of, or coated with, a material having the property of absorbing optical radiation. Then, parasitic optical radiation which passes through diaphragm 16 along paths which are inclined to path 17 are absorbed by internal wall 3d and thus will not reach receiver 11.

Preferably, electronic circuit 20 comprises self calibration means to set a signal intensity threshold each time the appliance is placed into operation. This intensity threshold permits detection of the presence of smoke between emitter 10 and receiver 11, or more generally any obstruction in path 17, with an optimum sensitivity despite aging or fouling of the optical system.

Figure 3:
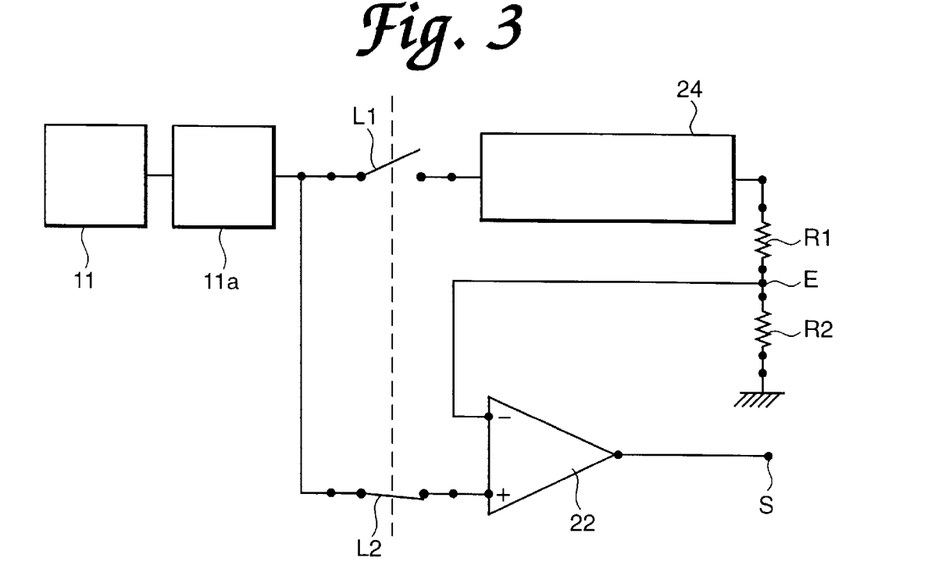
FIG. 3 is a circuit diagram of one embodiment of the electronic components of a device according to the invention.

FIG. 3 shows one example of an embodiment of electronic circuit 20 for performing the desired functions of the device according to the invention and including, in particular, self calibration means. Self calibration is achieved with the aid of a sample-and-hold device 24 connected to receiver 11 via a switch L1 and a signal conditioner 11a delivering a signal having a form which can be properly processed by the electronic components downstream of conditioner 11a. For example, conditioner 11a may amplify or attenuate the signal from receiver 11 to provide a signal which varies over a range suitable for processing by the electronic circuit components. Device 24 has an output connected to ground by the intermediary of a voltage divider constituted by a series connection of electric resistors R1 and R2. Electronic circuit 20 also comprises a comparator 22 having an inverting input connected to a point of connection E between resistors R1 and R2. The non-inverting input of comparator 22 is connected via a second switch L2 to the output of conditioner 11a. Thus, the non-inverting input of comparator 22 receives an input signal which is based on the output signal generated by receiver 11 and conditioned by conditioner 11a when switch L2 is closed. The voltage divider at the output of device 24 provides, at point E, a voltage proportional to, and lower than, the sampled voltage value currently being stored in device 24. This sampled voltage corresponds to a detection threshold, and particularly a smoke detection threshold.

Each time the cooking appliance, and specifically toaster 1, is placed into operation, switch L1 is placed in its closed state for a time interval corresponding to a sampling phase in order to supply a sampling voltage to device 24 and thus to produce a threshold voltage which is applied to the inverting input of comparator 22. Subsequent opening of switch L1 and simultaneous closing of switch L2 are controlled by a control and sequencing unit which is not shown in the drawing. This control and sequencing unit also suppresses an output signal from comparator 22 during the sampling phase, when switch L1 is closed. It will be appreciated that the control and sampling unit can be constituted by a structurally simple timing, or time delay, device that can be easily constructed based on principles well known in the control art.

The value of the threshold voltage appearing at connection point E depends directly on the intensity of the radiation signal initially received by receiver 11. The voltage present at connection point E is thus an instantaneous representation of the operating state of the optical system at the start of each cycle or of each use of the cooking appliance. Switch L1 can then be opened inasmuch as device 24 will continue to produce an output signal which maintains the voltage at connection point E at a substantially constant value during a relatively long period of time, sufficient to perform a cooking operation.

During a period of operation of a cooking appliance such as toaster 1, switch L2 remains closed and applies to the non-inverting input of comparator 22 a voltage corresponding in value to the intensity of the radiation received by receiver 11. A variation in the intensity of the radiation received by receiver 11 will influence the voltage applied to the non-inverting input of comparator 22. Thus, the voltage present at the output S of comparator 22 is directly representative of the presence or absence, in hot air column 18, corresponding to the detection zone, of a body or substance which can come from the cooking chamber (smoke) or from the outside (any object, including the user's hand).

During a cooking operation, when the appliance is functioning normally, the voltage at output S will be at a high level as long as the voltage at the non-inverting input of comparator 22 is greater than the threshold voltage supplied from connection point E. When, on the other hand, smoke or some intruding object at least partially blocks or obscures radiation which would otherwise be detected by receiver 11, the voltage applied to the non-inverting input of comparator 22 decreases and can reach a value at which the output S switches to a low value, or low level.

When the voltage at the output S takes on a low value, it is capable of immediately triggering the operation of means for terminating the supply of electric current to the cooking appliance. Depending on specific requirements, the functions of the inverting and non-inverting inputs of comparator 22 can be interchanged in a manner to reverse the direction of variation of the voltage at output S.

Device 24 thus permits application of a threshold potential to the connection point E, which potential is variable from one sampling phase to another, and, more precisely, takes account of dust or fouling of the optical means and/or aging of the optical means and the components of electronic circuit 20. Self calibration of the system in a device according to the invention is thus effectuated at each start of operation of an appliance provided with a safety device according to the invention.

This self calibration is necessary, taking into account that the safety device is not intended to serve as an optical barrier having an on-off mode of operation. Detection must be carried out in response to the presence of a totally opaque body, such as the user's hand, as well as bodies or substances, such as smoke, having varying degrees of opacity such that a certain proportion of radiation emitted by emitter 10 will still reach receiver 11. For detecting the presence of bodies or substances which are only partially opaque, it is necessary that the threshold value with which the detector signal is compared, corresponding to the presence of such an object or substance, must be reproducible even in the event of aging and/or fouling of components of the device, in order to maintain an adjusted and precise detection level.

Figure 4:
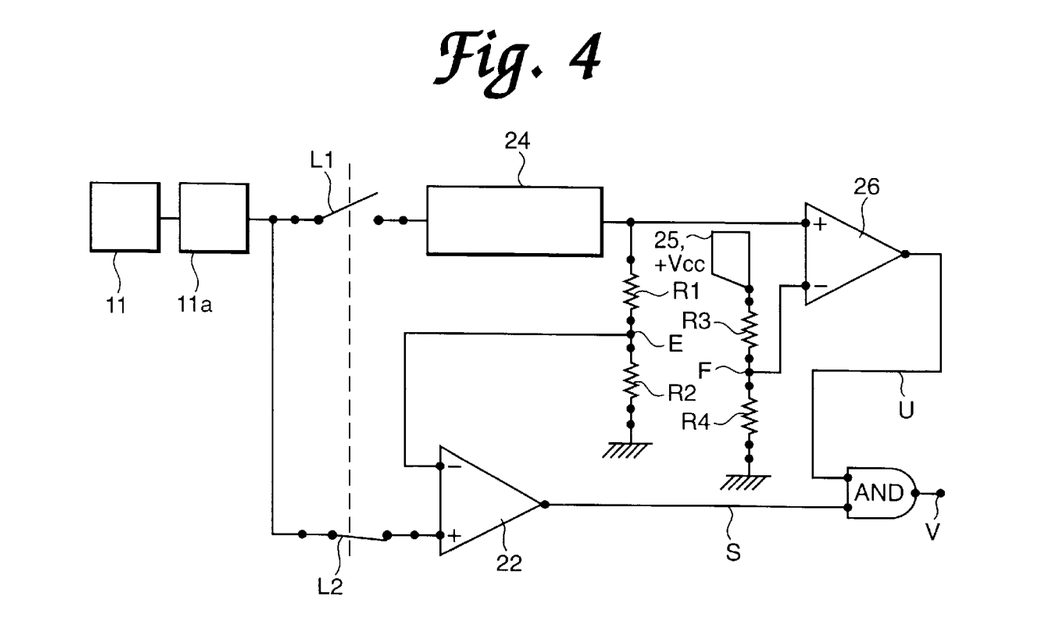
FIGS. 4 and 5 are circuit diagrams similar to those of FIG. 3 showing other embodiments of the electronic components of a device according to the invention.

FIG. 4 shows another embodiment of an electronic circuit 20 of a device according to the invention. This embodiment provides further improvements over the electronic circuit 20 shown in FIG. 3. The additional capabilities offered by the electronic circuit of FIG. 4 permit achievement of a complementary function, which is a monitoring of the potential applied to connection point E. Thus, a second comparator 26 has an inverting input connected to a point of connection F, this point of connection being between two resistors R3, R4 forming a second voltage divider. The second voltage divider is connected to a source 25 of a direct voltage having a constant value. The non-inverting input of comparator 26 is connected directly to the output of device 24.

Comparator 26 is thus arranged to deliver a monitoring, or control, signal U to a logical AND gate. The AND gate receives, at a second input, the signal on the output S of comparator 22. The AND gate will thus produce a validation output V when each of the signals U and S is at a high level.

Comparators 22 and 26 are devices, such as operational amplifiers, having a high open loop gain so that the output signal will have a high level as long as the voltage at the non-inverting input is larger in magnitude than the voltage at the inverting input. Comparators operate in this manner in order to assure that proper voltage levels are applied to the AND and OR gates.

In effect, the control signal U at the outlet of comparator 26 is applied to one input of the AND gate at the same time as the output signal S from comparator 22. Thus, the validation output signal V is at a high level when output signal S and control signal U are simultaneously at a high level. Such a situation corresponds to a normal operation of, and a normal output from, receiver 11.

When control signal U has a low level, this can be due to a very substantial or abnormal blocking of radiation to receiver 11 which is not due to an object or material in path 17. Such a situation results in the application to the non-inverting input of comparator 26 of a very low voltage which is below the potential corresponding to a minimum threshold, the latter corresponding to the potential at connection point F. Such utilization of a minimum threshold for the signal supplied by device 24 permits the supply of electric current to the electric appliance, such toaster 1, to be discontinued in the event of a very significant fouling or aging of the detector components, as a result of which receiver 11 may produce an output signal which is very weak and thus does not correspond to a signal indicating a normal and safe operation of the appliance. The voltage provided by source 25 as well as the resistance values of resistors R3 and R4 are, of course, selected to take into account slight deviations in the voltage delivered by device 24, which deviations can result from possible leakage currents. This system also permits detection of a malfunction in emitter 10.

The self calibrating means are thus associated with an electronic system which permits control of the intensity threshold of the signal received by receiver 11 at each start of operation of the cooking appliance. In addition, the self calibrating means permit consideration to be taken of variations over the course of time in the operating properties of the electronic and optical components. The resistance values of resistors R1, R2, R3 and R4 are selected as a function of the desired sensitivity of the system and of the required minimum detection threshold for an optimum operation of the smoke detection device according to the invention. The detection threshold can be adapted to the length of path 17 or to the output power of emitter 10, as well as to the sensitivity of receiver 11.

Figure 5:
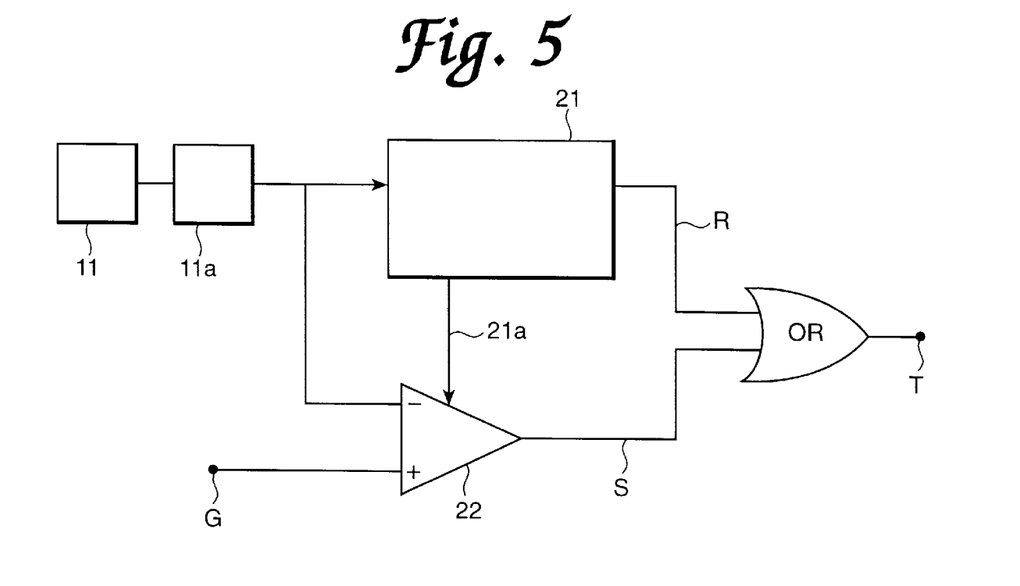

FIG. 5 shows a further embodiment of electronic circuit 20 of a device according to the invention. Here, electronic circuit 20 comprises a microprocessor 21 which is configured and programmed to analyze the signal received from receiver 11, as conditioned by conditioner 11a, and to supply operating power to comparator 22 and an output signal R to one input of an OR gate. The OR gate is also connected to receive output signal S from comparator 22. The inverting input of comparator 22 is connected to receive the output signal from conditioner 11a and the non-inverting input of comparator 22 is connected to a source of a fixed threshold voltage G, this threshold voltage being lower than the normal output signal from conditioner 11a. Microprocessor 21 is thus utilized for the detection of smoke by the intermediary of calculations which it performs and comparator 22 is utilized to detect interruption of a radiation beam due to some accident associated with the appliance. In such a case, it is essential to terminate the supply of operating current very quickly. This is obtained as a result of switching of output signal S from comparator 22 to a high level whenever such an interruption occurs. Thus, the OR gate generates an operation terminating control signal T when smoke is detected by the signal processing performed in microprocessor 21 or when an accidental interruption of the radiation beam is detected by the output signal from comparator 22. It is essential to utilize comparator 22 in that a device of this type reacts more rapidly to an abnormal situation than does microprocessor 21, the latter being required to effectuate certain calculations. The utilization of a microprocessor 21 which operates relatively slowly is envisioned in this embodiment of a safety device according to the invention.

The present invention thus provides a safety device which permits the detection of smoke, as well as detection of any potentially dangerous handling of a cooking appliance.

In the framework of processes according to the invention, it is in order to utilize radiation at least partially traversing a cooking environment. This makes it unnecessary to undertake any step for isolating the emitter-receiver system from ambient radiation or channeling of smoke.

The process according to the invention also involves utilizing on the one hand a radiation signal which is for example pulsed and on the other hand radiation, electronic or numeric filtering means for filtering and isolating the radiation signal received by receiver 11.

The implementation of such a process offers a great latitude in the arrangement of the means for carrying out the process on a cooking appliance.

In effect, the functioning of a device according to the invention permits elimination of any isolation or analysis chamber, which have heretofore been utilized for the detection of smoke. Elimination of such a chamber is necessary to allow the device to also detect objects which may approach the cooking chamber and which may endanger the operation of the appliance and/or the safety of the user. Thus, detection can be achieved efficiently even though the path 17 passes through a volume or an environment exposed to the influence of ambient radiation.

Advantageously, the electric signal emitted by emitter 10 is a pulsed radiation signal. It is thus in order to utilize a validation input 21a to supply operating power to comparator 22. The validation input 21a permits discrimination between a signal attenuation resulting on the one hand from a blockage of the radiation beam by an accidental obstruction of path 17, and on the other hand of an attenuation of the signal which is intrinsically linked to the pulsation thereof. In effect, a pulsed signal, for example in the form of a square wave, presents in a repetitive manner attenuations which can be differentiated from an accidental and random attenuation. The validation input 21a of comparator 22 is preferably controlled by microprocessor 21, which also controls emission of light from emitter 10. This permits synchronization of the validation input with the frequency of the radiation signal produced by emitter 10.

The pulsed signal in the form of a square wave can have different cyclic, or on-off, ratios. Other types of known pulsed signals are also within the spirit of the present invention.

The radiation signal utilized in a safety device according to the invention preferably has a frequency sufficiently different from 50 or 60 Hz to be capable of being filtered efficiently. By way of example, a frequency equal to or greater than 1500 Hz can be suitable. The electric signal delivered by receiver 11 thus has the form of square waves of the same frequency as the radiation signal. It is obvious that receiver 11 will be selected to be compatible with emitter 10, taking into account the nature of the radiation source represented by emitter 10. This radiation is preferably in the visible or infrared range and most preferably in a portion of the spectrum extending around 660 nm.

A pulsed signal can be easily distinguished from parasitic signals or radiation which may originate with any type of artificial light source or from sunlight. These latter types of parasitic radiation, to which it is necessary to add visible and infrared radiation emitted by heating elements of a cooking appliance such as a toaster, have a more or less substantial direct component which emitter 10 must be capable of ignoring. The utilization of a pulsed signal permits achievement of this goal. Detection of smoke or of an object by the intermediary of a device according to the invention results from a simple decrease in the amplitude of the peaks constituting a pulsed electrical signal from receiver 11.

Advantageously, electronic circuit 20 can be associated with numeric filtering means, for example with the aid of microprocessor 21.

Advantageously, toaster 1 shown in FIG. 1 having a safety device according to the invention comprises heating elements that can be supplied with a higher level of operating power than known appliances of the same type, to the extent that the risk of fire is remote. Such a toaster 1 can thus be adapted more easily to different types of bread.

The detection device according to the invention has a considerable interest to the extent that it permits attainment of good results despite a relatively large spacing of emitter 10 from receiver 11, which can amount to several tens of centimeters or more. By way of example, path 17 can have a length of the order of 30 cm.

Contrary to all expectations, attenuation of the signal received by receiver 11 as a result of the relatively long length of path 17 does not adversely affect the reliability of the device.

In accordance with further embodiments of the invention, the means for processing the signal received by receiver 11 can be constructed to effect a synchronous demodulation to extract the useful signal in the presence of noise.

A suitable synchronous demodulation circuit can be constructed on the basis of principles well known in the art. Synchronous demodulators are described, for example, in the periodical *Techniques de l'Engénieur*, Vol. E311–E3480-§ 3.211 (September, 1997).

Another advantage of toaster 1 containing a device according to the invention resides in the fact that it permits detection, due to the smoke emitted, of excessive toasting as a result of a poor adjustment, or regulation, of the appliance for a given type of bread. The heating elements of the toaster 1 are shut off before the slices of bread become unduly burned. These slices of bread thus remain edible to the extent that any high toasting setting provokes a liberation of smoke, before burning or scorching.

Another advantage of the toaster shown in FIG. 1 resides in the possibility of instantaneously halting toasting and possibly triggering ejection of the bread slices in response to a simple interruption of the radiation beam generated by the optical system.

The safety device according to the invention also presents the advantage of being able to be utilized as a safety means for preventing a user from being burned or electrocuted, as already explained.

The safety device according to the invention can also remain active after the supply of heating power to the elements has been terminated and/or after the ejection of bread slices, for as long as the hot parts of the appliance have a temperature above a given limit. In such a case, means for momentarily inhibiting or initializing the detection system are necessary in order to proceed with a new cooking operation. The detection device according to the invention can equally be arranged in a removable subassembly which one attaches to or removes from a conventional toaster 1. The smoke detection device can then be arranged in a structure attachable to housing 3 and can be provided with an audible alarm means.

The safety device according to the invention can equally be associated with electric ovens for the purpose of detecting scorching or in range hoods equipped with an exhaust for automatic adaptation of the exhaust force to the quantity of smoke detected.

This application relates to subject matter disclosed in French Application Number 96 12522, filed on Oct. 9, 1996, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Safety device comprising a radiation emitter, a radiation receiver disposed for receiving radiation which is produced by said emitter and which traverses a radiation path between said emitter and said detector, said detector producing an output signal representative of the quantity of radiation received by said detector, and electronic means coupled to said detector for analyzing the output signal produced by said detector and identifying a reduction in the magnitude of the output signal as a result of an obstruction in the radiation path, wherein said emitter and said detector are mounted on a cooking appliance at locations such that the radiation path is exposed to ambient radiation in the vicinity of the cooking appliance.

2. Device according to claim 1 further comprising an element enclosing a portion of the radiation path, said element having a bottom at which said detector is mounted.

3. Device according to claim 2 wherein said element has an opening which is spaced from said detector, and further comprising a diaphragm disposed in front of said opening.

4. Device according to claim 1 wherein said emitter and said detector are disposed such that said radiation path extends across a cooking region defined by the cooking appliance.

5. Device according to claim 1 wherein said electronic means comprise self calibration means for establishing, each time the cooking appliance is placed in operation, a threshold with which the output signal from said detector is compared.

6. Device according to claim 5 wherein said electronic means further comprise a system for monitoring the value of the threshold.

7. Device according to claim 1 further comprising a system for forming radiation emitted from said emitter into a beam.

8. Device according to claim 7 wherein the beam is brought to a focus at said detector.

9. Device according to claim 7 wherein the beam has a collimated form between said emitter and said detector.

10. Device according to claim 1 wherein the cooking appliance has a cooking chamber provided with an opening for introduction of an item into the cooking chamber, and said emitter and said detector are mounted above the opening and outside of the cooking chamber.

11. Device according to claim 1 wherein said electronic means produce a signal to terminate operation of the cooking appliance in response to the identification of a reduction in the magnitude of the output signal as a result of an obstruction in the radiation path.

12. Device according to claim 1 wherein the obstruction comprises a vapor.

13. In combination, a toaster and a safety device, said safety device comprising an optical emitter, an optical detector disposed for receiving radiation produced by said emitter and traversing a radiation path between said emitter and said detector, said detector producing an output signal representative of the quantity of radiation received by said detector, and electronic means coupled to said detector for analyzing the output signal produced by said detector and identifying a reduction in the magnitude of the output signal as a result of an obstruction in the radiation path, wherein said emitter and said detector are mounted on said toaster at locations such that the radiation path is exposed to ambient radiation in the vicinity of said toaster.

14. The combination according to claim 13 further comprising an element enclosing a portion of the radiation path, said element having a bottom at which said detector is mounted.

15. The combination according to claim 14 wherein said element has an opening which is spaced from said detector, and further comprising a diaphragm disposed in front of said opening.

16. The combination according to claim 13 wherein said emitter and said detector are disposed such that said radiation path extends across a cooking region defined by said toaster.

17. The combination according to claim 13 wherein said electronic means comprise self calibration means for establishing, each time said toaster is placed in operation, a threshold with which the output signal from said detector is compared.

18. The combination according to claim 17 wherein said electronic means further comprise a system for monitoring the value of the threshold.

19. The combination according to claim 13 further comprising a system for forming radiation emitted from said emitter into a beam.

20. The combination according to claim 19 wherein the beam is brought to a focus at said detector.

21. The combination according to claim 19 wherein the beam has a collimated form between said emitter and said detector.

22. The combination according to claim 13 wherein said toaster has a toasting chamber provided with an opening for introduction of an item into said toasting chamber, and said emitter and said detector are mounted above the opening and outside of said toasting chamber.

23. The combination according to claim 13 wherein said electronic means produce a signal to terminate operation of said toaster in response o the identification of a reduction in the magnitude of the output signal as a result of an obstruction in the radiation path.

24. The combination according to claim 13 wherein the obstruction comprises a vapor.

25. Process for detecting the presence of a material having a certain opacity, said process comprising directing a radiation signal along a radiation path, recognizing attenuation experienced by the radiation signal due to the presence of such material in the path, and controlling the operation of an appliance in response to such a recognition, which appliance encloses a cooking environment, wherein: the radiation path extends at least partially outside the cooking environment; the radiation signal is composed of a series of discrete pulses produced by a radiation emitter; and said step of recognizing is carried out with the aid of a radiation detector associated with means for filtering and isolating the radiation signal at the receiver.

26. Process according to claim 25 wherein the radiation pulses have a repetition rate of at least 1500 Hz.

27. Process according to claim 25 performed adjacent a toasting region of a toaster.

28. Process according to claim 25 wherein the material being detected comprises a vapor.

* * * * *